United States Patent [19]

Sirrenberg et al.

[11] 4,225,618
[45] Sep. 30, 1980

[54] COMBATING PLANT PESTS WITH N-(ω-CHLORO-ALKANOYL)-N'-TRI-FLUOROMETHYLPHENYL-UREAS

[75] Inventors: Wilhelm Sirrenberg, Sprockhoevel; Erich Klauke, Odenthal-Hahnenberg; Wilhelm Brandes, Leichlingen; Peter Roessler, Bensberg-Refrath, all of Fed. Rep. of Germany

[73] Assignee: Bayer Aktiengesellschaft, Leverkusen, Fed. Rep. of Germany

[21] Appl. No.: 10,289

[22] Filed: Feb. 8, 1979

[30] Foreign Application Priority Data

Feb. 14, 1978 [DE] Fed. Rep. of Germany ....... 2806213

[51] Int. Cl.$^3$ ..................... A01N 47/28; C07C 127/00
[52] U.S. Cl. ................................ 424/322; 260/553 A; 260/553 E
[58] Field of Search .................... 424/322; 260/553 A, 260/553 E

[56] References Cited

U.S. PATENT DOCUMENTS 2,801,200  7/1957  Hackmann ..................... 424/322
3,184,507  5/1965  Scherer et al. ................... 260/553 E
4,101,575  7/1978  Enders et al. ..................... 260/553 E Primary Examiner—Leonard Schenkman
Attorney, Agent, or Firm—Sprung, Felfe, Horn, Lynch & Kramer

[57] ABSTRACT

N-(ω-chloroalkanoyl)-N'-trifluoromethylphenyl-ureas of the formula

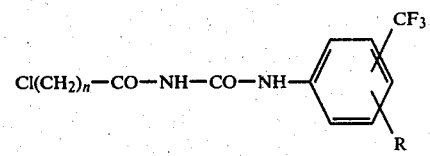

in which
n is 1 or 2, and
R is halogenoalkyl or halogen, and can also be hydrogen when n is 2, which possess arthropodicidal and fungicidal properties.

3 Claims, No Drawings

COMBATING PLANT PESTS WITH N-(ω-CHLORO-ALKANOYL)-N'-TRIFLUOROME-THYLPHENYL-UREAS

The present invention relates to and has for its objects the provision of particular new N-(ω-chloroalkanoyl)-N'-trifluoromethylphenyl-ureas which possess arthropodicidal and fungicidal properties, active compositions in the form of mixtures of such compounds with solid and liquid dispersible carrier vehicles, and methods for producing such compounds and for using such compounds in a new way especially for combating pests, e.g. insects, acarids and fungi, with other and further objects becoming apparent from a study of the within specification and accompanying examples.

It is known that N-halogenoalkylthio-phthalimides, for example N-trichloromethylthio-tetrahydrophthalimide, have fungicidal properties and are used worldwide as commercial products for plant protection (see R. Wegler, Chemie der Pflanzenschutz- und Schädlingsbekämpfungsmittel (Chemistry of Plant Protection Agents and Agents for Combating Pests), volume 2, page 108, Springer-Verlag Berlin/Heidelberg/New York, 1970). However, the action of such compounds is not always completely satisfactory, especially when low amounts are used.

Active compounds which inhibit the metamorphosis of Arthropoda have only recently been of interest in plant protection. An example which may be mentioned here is 2,2-dimethyl-6-methoxybenzopyrane (Chem. Eng. News 54, 19–20 (1976)).

The present invention now provides, as new compounds, the N-(ω-chloroalkanoyl)-N'-trifluoromethyl-phenyl-ureas of the general formula

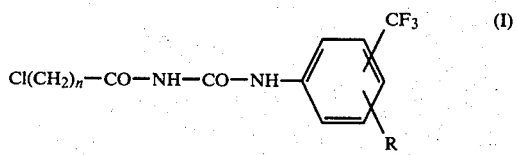

in which

R represents halogenoalkyl or halogen, and can also represent hydrogen if n represents the number 2, and n represents the number 1 or 2, Preferably, R represents trifluoromethyl, chlorine or, provided that n represents the number 2, hydrogen.

Surprisingly, the N-(ω-chloroalkanoyl)-N'-trifluoromethylphenyl-ureas according to the invention possess a considerably better fungicidal action than the N-halogenoalkylthiophthalimides, of the same type of action, known from the state of the art. The development-inhibiting action on Arthropoda is also of interest. The substances according to the invention thus represent an enrichment of the art.

The present invention also provides a process for the production of an N-(ω-chloroalkanoyl)-N'-trifluoromethylphenyl-urea of the formula (I) in which (a) an ω-chloroalkanoyl isocyanate of the general formula $$Cl-(CH_2)_n-CO-NCO \qquad (II),$$

wherein n has the meaning stated above, is reacted with a trifluoromethyl-aniline of the general formula

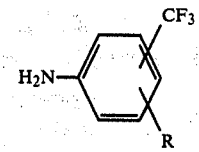

in which

R has the meaning stated above, optionally in the presence of an inert solvent or diluent, or (b) an ω-chloroalkanoyl chloride or the corresponding anhydride, of the general formula

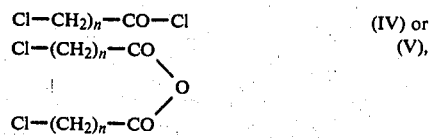

wherein n has the meaning stated above, is reacted with a trifluoromethylphenyl-urea of the general formula

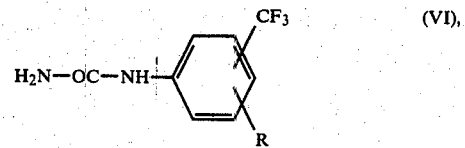

in which

R has the meaning stated above, optionally in the presence of an acid-acceptor and optionally in the presence of an inert solvent or diluent, or (c) an ω-chloroalkanoyl-amine or the general formula $$Cl-(CH_2)_n-CO-NH_2 \qquad (VII),$$

in which n has the meaning stated above, is reacted with a trifluoromethylphenyl isocyanate of the general formula

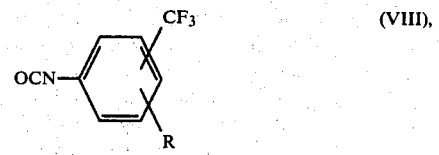

in which

R has the meaning stated above, optionally in the presence of an inert solvent or diluent and optionally in the presence of a catalyst.

If chloroacetyl isocyanate and 2-trifluoromethyl-4-chloro-aniline are used as starting materials according to process variant (a), ω-chloropropionyl chloride and 4-trifluoromethylphenyl-urea, in the presence of a base, are used as starting materials according to process variant (b) and chloroacetamide and 3,5-bis-trifluoromethylphenyl isocyanate are used as starting materials according to process variant (c), the course of the reactions can be represented by the equations which follow:

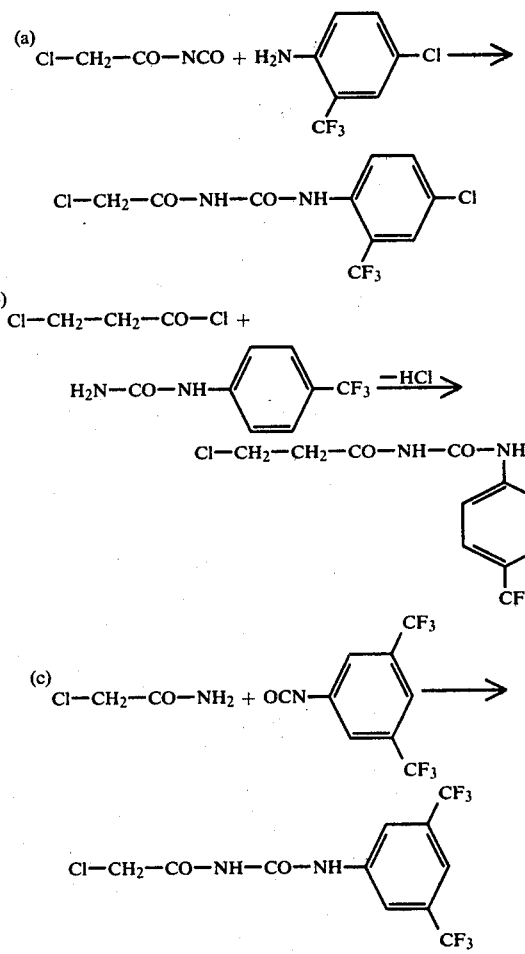

ω-Chloroalkanoyl isocyanates (II) to be used as starting materials are known and can be prepared by processes which are known from the literature (see J. Org. Chem. 27, (1962), 3742 and J. Org. Chem. 28 (1963), 1805). Thus, for example, chloroacetamide can be reacted with oxalyl chloride at 80° C. and, after a reaction time of 24 hours, chloroacetyl isocyanate is obtained in a yield of 64% of theory, in addition to carbon monoxide and hydrogen chloride.

Examples which may be mentioned are chloroacetyl isocyanate and ω-chloro-propionyl isocyanate.

Trifluoromethyl-anilines of the formula (III), which are also to be used as starting materials, are likewise known and can be prepared by processes which are known from the literature (see Adv. Fluorine Chem. 6 (1970), 1). Thus, for example, the methyl group of o-nitrotoluene can be chlorinated to give 1-trichloromethyl-2-nitrobenzene, reaction with hydrogen fluoride leads to the corresponding trifluoromethyl compound and reduction of the latter in the customary manner gives o-trifluoromethyl-aniline. The anilines of the formula (III) can be converted to the trifluoromethylphenyl-ureas of the formula (V) or into the trifluoromethylphenyl isocyanates of the formula (VIII) by methods which are generally customary (see Indian J. Appl. Chem. 35, 129–130 (1972)), for example by reaction with alkali metal cyanates or with phosgene.

Examples which may be mentioned are: 2-trifluoromethyl-, 4-trifluoromethyl-, 2,3-bis-trifluoromethyl-, 2,4-bis-trifluoromethyl-, 2,5-bis-trifluoromethyl-, 2,6-bis-trifluoromethyl-, 3,4-bis-trifluoromethyl-, 3,5-bis-trifluoromethyl-, 2-trifluoromethyl-3-chloro-, 2-trifluoromethyl-4-chloro-, 2-trifluoromethyl-5-chloro-, 2-trifluoromethyl-6-chloro-, 3-trifluoromethyl-2-chloro-, 3-trifluoromethyl-4-chloro-, 3-trifluoromethyl-5-chloro-, 3-trifluoromethyl-6-chloro-, 4-trifluoromethyl-2-chloro- and 4-trifluoromethyl-3-chloro-aniline or -phenylurea or -phenyl isocyanate.

The ω-chloroalkanoyl chlorides of the formula (IV), the corresponding anhydrides of the formula (V) and the corresponding amides of the formula (VII), which are also to be used as starting materials, are generally known as industrial intermediate products.

Examples which may be mentioned are: chloroacetic acid chloride, anhydride and amide and ω-chloropropionic acid chloride, anhydride and amide.

The process variants for the preparation of the N-(ω-chloroalkanoyl)-N'-trifluoromethylphenyl-ureas according to the invention are preferably carried out using suitable solvents or diluents. Possible solvents and diluents are virtually all the inert organic solvents, especially aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methylisobutyl ketone; and nitriles, such as acetonitrile and propionitrile.

The reaction temperature can be varied within a substantial range in all the process variants. In general, the reaction is carried out at from 0° to 150° C., preferably at from 20° to 120° C. A temperature range of from 30° to 80° C. is particularly preferred for process variant (a).

The reactions are in general carried out under normal pressure.

The customary inorganic or organic acid-binding agents can be used as the acid-binding agent in process variant (b), especially the alkali metal hydroxides and alkali metal carbonates, for example sodium hydroxide and potassium carbonate, and tertiary amines, for example triethylamine or pyridine.

Catalysts can be used in process variant (c). Organic bases, such as, for example, triethylamine, or metal salts, such as, for example, tin (II) compounds, may be mentioned here.

The starting compounds are preferably employed in equimolar amounts for carrying out the preparation processes. An excess of one or the other of the reactants provides no substantial advantages. In general, the reactants are brought together in one of the solvents indicated and an auxiliary base is added if appropriate. After stirring the mixture for one or more hours in the temperature range indicated and then cooling at room temperature, the products, which are obtained as crystals, can be isolated by filtration. The new products are characterized by their melting points.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Dueteromycetes.

The active compounds according to the invention can be used against parasitic fungi and bacteria which infect above-ground parts of plants or attack the plants through the soil, as well as against seed-borne pathogens.

The good tolerance by plants makes it possible to use the compounds against fungal plant diseases, by treating the standing crop plants or individual parts thereof, or the seed or also the cultivated soil. The active compounds are particularly active against species of Venturia and against those fungi which damage cereal crops.

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Procellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix, Pemphigus* spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysis ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa Jecemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose. Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

For the treatment of seed, amounts of active compound of 10 mg to 10 g, especially 100 mg to 3 g, per kilogram of seed are generally used. For the treatment of soil, which can be effected over the whole area, over strips or at certain points, active compound concentrations of 1 to 1,000 g of active compound per m$^3$ of soil, especially 10 to 200 g per m$^3$, are generally employed at the location of the intended action.

The present invention also provides a fungicidal or arthropodicidal composition containing as active ingredient a compound of the present invention in admixture with a solid or liquefied gaseous diluent or carrier or in admixture with a liquid diluent or carrier containing a surface-active agent.

The present invention also provides a method of combating fungi or arthropods (especially insects) which comprises applying to the fungi or arthropods, or to a habitat thereof, a compound of the present invention alone or in the form of a composition containing as active ingredient a compound of the present invention in admixture with a diluent or carrier.

The present invention further provides crops protected from damage by fungi or arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

(a) Precursor: Cl—CH$_2$—CO—NCO

The compound was prepared from chloroacetamide and oxalyl chloride according to statements in the literature (J. Org. Chem. 27, 3742 (1962) and J. Org. Chem. 28, 1805 (1963)). Boiling point 43° C./13 mm Hg.

(b)

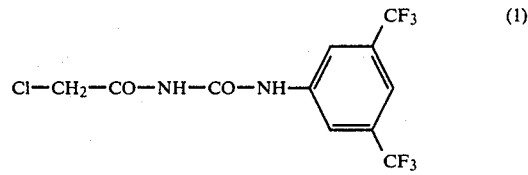

22.9 g (0.1 mol) of 3,5-bis-trifluoromethyl-aniline were dissolved in 150 ml of dry toluene. 11.9 g (0.1 mol) of chloroacetyl isocyanate in 50 ml of dry toluene were added. The mixture was stirred at 50° C. for 1 hour and then cooled to room temperature. The product which had precipitated was filtered off and rinsed with toluene/ligroin 1:2 and then dried. 26 g (74.5% of theory) of N-(3,5-bis-trifluoromethylphenyl)-N'-(chloroacetyl)-urea with a melting point of 170° C. were thus obtained.

EXAMPLE 2

(a) Cl—CH$_2$—CH$_2$—CO—NCO, boiling point 47° C./5 mm Hg, was prepared analogously to Example 1(a).

(b)

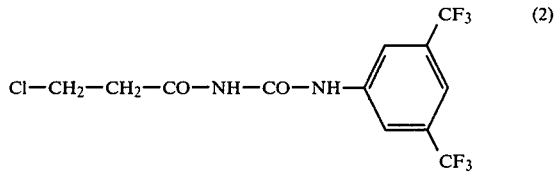

11.45 g (0.05 mol) of 3,5-bis-trifluoromethylaniline were dissolved in 80 ml of dry toluene, and 6.7 g (0.05 mol) of β-chloropropionyl isocyanate in 20 ml of dry toluene were added. The mixture was stirred at 60° C. for 1 hour, the solvent was distilled off in vacuo and the residue was taken up in petroleum ether. The crystalline product was filtered off and dried. 14.5 g (80.5% of theory) of N-(3,5-bis-trifluoromethyl-phenyl)-N'-(β-chloropropionyl)-urea, which melts at 175° C., were obtained.

The purity and identity of the products were confirmed by elementary analysis and by the NMR spectrum. The yields were not optimized.

The following compounds of the general formula

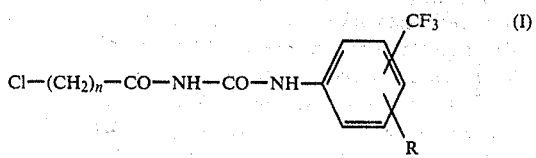

were prepared in a corresponding manner:

| Compound No. | n | CF$_3$ position | R | Melting point (°C.) | Yield (% of theory) |
|---|---|---|---|---|---|
| 3 | 1 | 3 | 4-CF$_3$ | 113 | 77.5 |
| 4 | 1 | 2 | 4-CF$_3$ | 156 | 57.5 |
| 5 | 1 | 3 | 4-Cl | 162 | 76 |
| 6 | 1 | 5 | 2-Cl | 170 | 70 |
| 7 | 1 | 2 | 4-Cl | 147 | 66.5 |
| 8 | 1 | 4 | 2-Cl | 170 | 66.5 |
| 9 | 2 | 3 | H | 127 | 55 |
| 10 | 2 | 4 | H | 172 | 83.5 |
| 11 | 2 | 3 | 4-CF$_3$ | 161 | 82.5 |
| 12 | 2 | 2 | 4-CF$_3$ | 176 | 94 |
| 13 | 2 | 3 | 4-Cl | 178 | 59 |
| 14 | 2 | 5 | 2-Cl | 157 | 65 |
| 15 | 2 | 2 | 4-Cl | 183 | 94 |
| 16 | 2 | 4 | 2-Cl | 198 | 89.5 |
| 17 | 2 | 4 | 3-Cl | 167 | 85 |

The yields were not optimized.

The products could also be prepared by reacting trifluoromethyl-phenyl-ureas with the appropriate anhydrides or with the corresponding acid halides in the presence of a base, or by reacting the ω-halogen-acid amides with the appropriate trifluoromethyl-phenyl isocyanates.

The activity of the compounds of this invention is illustrated by the following examples wherein the compounds according to the present invention are each identified by the number (given in brackets) from the preparative examples hereinabove:

EXAMPLE 3

Mycelium growth test
Nutrient medium used:
20 parts by weight of agar-agar
200 parts by weight of potato decoction
5 parts by weight of malt
15 parts by weight of dextrose
5 parts by weight of peptone
2 parts by weight of disodium hydrogen phosphate
0.3 parts by weight of calcium nitrate
Composition of the solvent mixture:
0.19 part by weight of acetone
0.01 part by weight of emulsifier (alkylaryl polyglycol ether)
1.80 parts by weight of water
Ratio of solvent mixture to nutrient medium:
2 parts by weight of solvent mixture
100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42 deg.C.) and was then poured into Petri dishes of 9 cm diameter. Control plates to which the preparation had not been added were also set up.

When the nutrient medium had cooled and solidified, the plates were inoculated with the species or organisms stated hereinbelow and incubated at about 21 deg.C.

Evaluation was carried out after 4–10 days, dependent upon the speed of growth of the organisms. When evaluation was carried out the radial growth of the organism on the treated nutrient media was compared with the growth on the control nutrient medium.

Evaluation of the test showed that, for example, the compound (1) had a good action against the species of fungi *Rhizoctonia solani, Cochliobolus miyabeanus, Pyricularia oryzae, Helminthosporium gramineum, Mycosphaerella musicola, Phytophthora cactorum* and *Pellicularia sasakii*.

EXAMPLE 4

*Fusicladium* test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20 degrees C. and at a relative atmospheric humidity of 70%. They were then inoculated with an aqueous conidium suspension of the apple scab causative organism (*Fusicladium dendriticum*) and incubated for 18 hours in a humidity chamber at 18–20 degrees C. and at a relative atmospheric humidity of 100%.

The plants were then brought into a greenhouse again for 14 days. 15 days after inoculation, the infection of the seedlings was determined.

Evaluation of the test showed that, for example, the compound (1) had a superior action to the comparison preparation indicated in the prior art.

As already mentioned, the compounds according to the invention inhibit the development of arthropods (*Arthropoda*). The inhibiting action of the compounds according to the invention on the metamorphosis of Anthropoda is illustrated in the following examples, without a limitation with regard to the spectrum of action of these compounds being intended.

In the following examples, which relate to the development-inhibiting action of the active compounds, the morphological changes, such as half-pupated insects, incompletely slipped larvae or caterpillars, defective wings, pupal cuticula in imagos, and the like, were rated as malformations over the entire stated development of the test insects. The sum of the morphological malformations, together with the insects killed during shedding or during metamorphosis was determined as a percentage of the total number of test insects employed.

EXAMPLE 5

Development-inhibiting action/*Aedes aegypti* test
Test insects: *Aedes aegypti* (larvae in the 3rd stage of development)
Number of test insects. 20 specimens Solvent: 10 parts by weight of acetone Emulsifier: 1 part by weight of alkylaryl polyglycol ether To produce a suitable preparation of active compound, 2 parts by weight of active compound were mixed with the stated amount of solvent and emulsifier and with sufficient water to produce a mixture containing 100 ppm, which was diluted with water to the desired concentration.

The test insects were introduced into 90 ml of an active compound preparation of the desired concentration and were observed until the imago slipped. As a control, test insects were introduced into a mixture of solvent, emulsifier and water of the corresponding concentration and observed until the imago slipped.

In this test, for example, compound (1) showed a superior action compared to the prior art.

EXAMPLE 6

Development-inhibiting action/Laphygma caterpillar test

Test insects: *Laphygma frugiperda* (caterpillars)

Feed: 1 cm thick disc of 3 cm diameter, of an air-dried artificial feed based on shredded beans, yeast, vitamin mixture, leaf powder, agar and preservative Solvent: 10 parts by weight of acetone Emulsifier: 1 part by weight of alkylaryl polyglycol ether To produce a suitable preparation of active compound, 2 parts by weight of active compound were mixed with the stated amount of solvent and emulsifier and with sufficient water to give a 1% strength mixture, which was diluted with water to the desired concentration.

Each test insect was placed on a separate feed disc moistened with 1.5 ml of active compound preparation of the desired concentration, and was observed until the imago slipped.

As a control, test insects were each placed on separate feed discs moistened with 1.5 ml of a mixture of solvent, emulsifier and water of the corresponding concentration and observed until the imago slipped.

In this test, for example, a compound (1) showed a superior action compared to the prior art.

It will be appreciated that the instant specification and examples are set forth by way of illustration and not limitation, and that various modifications and changes may be made without departing from the spirit and scope of the present invention.

We claim:

1. N-(3,5-Bis-trifluoromethylphenyl)-N'-(chloroacetyl)-urea of the formula

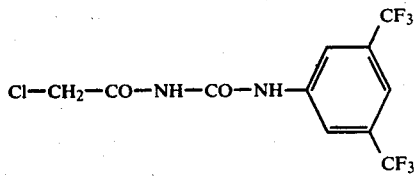

2. An arthropodicidal or fungicidal composition containing as active ingredient an arthropodicidally or fungicidally effective amount of a compound according to claim 1 in admixture with a diluent.

3. A method of combating arthropods or fungi which comprises applying to the arthropods or fungi, or to a habitat thereof, an arthropodicidally or fungicidally effective amount of a compound according to claim 1.